United States Patent [19]

Saadatmanesh et al.

[11] Patent Number: 5,467,483
[45] Date of Patent: Nov. 21, 1995

[54] SURGICAL GLOVE WITH REMOVAL MEANS PROTECTED FROM CONTAMINATION

[76] Inventors: Hamid Saadatmanesh, 5121 E. Paseo Del Bak, Tucson, Ariz. 85718; Mohammad R. Ehsani, 5630 E. Via Arbolada, Tucson, Ariz. 85715

[21] Appl. No.: 178,898

[22] Filed: Jan. 7, 1994

[51] Int. Cl.$^6$ .................................................. A41D 19/00
[52] U.S. Cl. ........................... 2/161.7; 2/162; 2/168
[58] Field of Search .................. 2/161.6, 161.7, 2/162, 168, 16, 158, 159, 160, 161.8, 167, 169, 901

[56] References Cited

U.S. PATENT DOCUMENTS

| | | | |
|---|---|---|---|
| 2,325,482 | 7/1943 | Curran | 2/159 |
| 3,110,035 | 11/1963 | Hue | 2/168 |
| 3,548,413 | 12/1970 | Jackson | 2/161.6 |
| 3,555,564 | 1/1971 | Miskell et al. | 2/168 |
| 3,728,739 | 4/1973 | Semp | 2/168 |
| 4,064,564 | 12/1977 | Casey | 2/168 |
| 4,099,270 | 7/1978 | Jabour | 2/168 |
| 4,845,780 | 7/1989 | Reimers et al. | 2/160 |
| 4,876,747 | 10/1989 | Coffey et al. | 2/168 |
| 4,884,300 | 12/1989 | Vistins | 2/162 |
| 4,971,233 | 11/1990 | Keenan | 223/111 |
| 5,020,159 | 6/1991 | Hellickson | 2/158 |
| 5,020,160 | 6/1991 | Cano | 2/161.7 |
| 5,317,760 | 6/1994 | Best | 2/161.7 |
| 5,365,608 | 11/1994 | Flick | 2/161.7 |

FOREIGN PATENT DOCUMENTS 2832347 2/1980 Germany ........................... 2/168

Primary Examiner—C. D. Crowder
Assistant Examiner—Amy B. Vanatta
Attorney, Agent, or Firm—Antonio R. Durando; Harry M. Weiss

[57] ABSTRACT

A glove having a wrist portion that contains a removable protective cover over a gripping means. The cover is impermeable to contamination and protects the gripping means from exposure to any infectious substance that may come into contact with the glove during use. After use, the glove is taken off by first removing the protective cover and then using the clean gripping means to pull the glove off. If at least one glove in a pair is equipped with the protective cover of the invention and both gloves comprise gripping means, both gloves can be removed without contact by unprotected fingers with contaminated portions of either glove.

20 Claims, 1 Drawing Sheet

SURGICAL GLOVE WITH REMOVAL MEANS PROTECTED FROM CONTAMINATION

BACKGROUND OF THE INVENTION

1. Field of the Invention

This invention pertains to the general field of protective gloves, such as for surgeons, paramedics, dentists, laboratory technicians, and the like. In particular, it provides a new means for protecting a user from contamination during removal of the gloves after a surgical or other procedure.

2. Description of the Prior Art

Protective gloves are common for all activities that require the handling of hazardous, offensive or harmful material. Thus, they are used in kitchens to avoid excessive exposure to water and soap during dish washing, as well as in all kinds of industrial activities to protect against the effects of chemicals and similarly potentially-damaging substances.

Various patents have been obtained covering different kinds of gloves with specific useful features. For example, U.S. Pat. Nos. 3,110,035, No. 3,555,564, No. 4,099,270, No. 4,845,780 and No. 4,884,300 describe gloves having improved wear and improved means for tightly securing the cuff around the arm of a user; U.S. Pat. Nos. 3,728,739 and No. 4,064,564 disclose lubricated gloves to prevent deterioration during storage and to facilitate emplacement; and U.S. Pat. Nos. 4,971,233 and No. 5,020,159 describe gloves with special donning and handling means.

Protective surgical gloves have been used by surgeons and other health-care professionals for decades to avoid exchange of contaminants with patients during surgical and other procedures. Such use has increased rapidly throughout the world during the last few years, especially as a result of the spread of serious bacterial and viral infections. In some cases, such as when there is a risk of communicating the AIDS virus, it is imperative that contamination prevention be assured.

The most apparent problem with the latex-type gloves used routinely by surgeons and other health-care practitioners is that they cannot be removed without some contact with the skin of the user. Thus, if a glove has been infected during surgery, for example, there is a possibility that a contaminated portion of the glove may touch the surgeon's skin during removal even if extreme caution is used. Addressing this danger, U.S. Pat. No. 4,876,747 to Coffey et al. (1989) describes a glove with a raised loop attached to the wrist portion, so that the glove can be removed more easily by hooking the loop and peeling the glove off, thus preventing contact with the user's skin.

A remaining potential problem with this type of glove is the necessity to use a separate hooking tool in order to ensure the protective effectiveness of the glove. If the tool is misplaced or not available for any reason, it is likely that a wearer would resort to using his or her fingers to pull the gloves off. Thus, while the first glove of a worn pair could be hooked and removed with a glove-protected finger, the second glove would probably be removed by using the first hand's naked fingers. This procedure still leaves the wearer exposed to a risk of contamination. Therefore, there still exists a need for a glove that incorporates effective self-contained means for removal that protect the user under all circumstances.

BRIEF SUMMARY OF THE INVENTION

One objective of this invention is the development of a novel means for removing a glove with full protection from contamination under all circumstances.

Another objective of the invention is a glove having protective removal means that does not require the use of a separate removal tool.

A further goal of the invention is a glove that is suitable for manufacture in latex or similar elastomeric impervious material.

A final objective is the easy and economical manufacture of the glove by using commercially available components and materials, modified to fit the requirements of this invention.

Therefore, according to these and other objectives, the present invention consists of a glove having a wrist portion that contains a removable protective cover over a gripping means. The cover is impermeable to contamination and protects the gripping means from exposure to any infectious substance that may come into contact with the glove during use. After use, the glove is taken off by first removing the protective cover and then using the clean gripping means to pull the glove off. If at least one glove in a pair is equipped with the protective cover of the invention and both gloves comprise gripping means, both gloves can be removed without contact by unprotected fingers with contaminated portions of either glove.

Various other purposes and advantages of the invention will become clear from its description in the specification that follows and from the novel features particularly pointed out in the appended claims. Therefore, to the accomplishment of the objectives described above, this invention consists of the features hereinafter illustrated in the drawings, fully described in the detailed description of the preferred embodiment and particularly pointed out in the claims. However, such drawings and description disclose but one of the various ways in which the invention may be practiced.

DETAILED DESCRIPTION OF THE INVENTION

The heart of this invention lies in the recognition that especially designed tabs, loops or other gripping mechanisms incorporated in the wrist portion of a glove are not sufficient to prevent contact of the glove's exterior with a user's skin. An additional layer of protection is required, so that the gripping mechanism itself is prevented from contacting contaminated portions of the glove and its cleanliness is maintained for later safe contact with the bare hands of a user.

Figure 1:
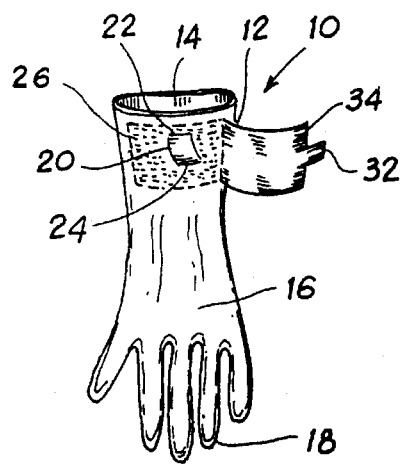
FIG. 1 is a perspective view of a glove according to this invention showing a gripping means in the wrist portion thereof for pulling the glove off after use and a protective cover (shown open) to prevent contamination of the gripping means.
Figure 3:
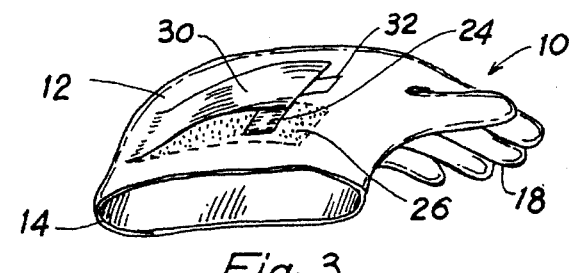
FIG. 3 is a perspective end view of the glove of FIG. 1 illustrating the gripping means in the wrist portion exposed by the open protective cover and showing adhesive means whereby the cover is attached to the glove.
Figure 4:
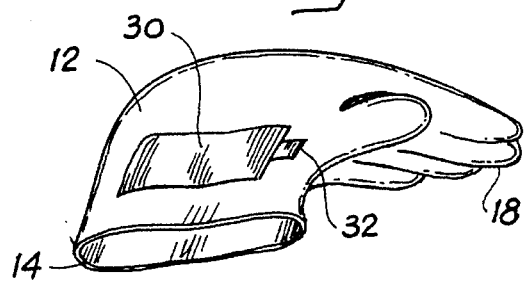
FIG. 4 is the same view of FIG. 3 showing a different embodiment of the invention wherein the protective cover is detachable from the glove.
Figure 2:
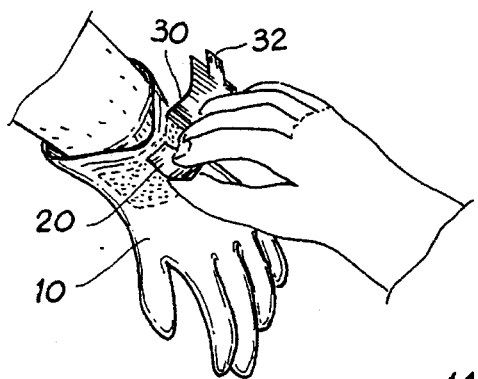
FIG. 2 is a perspective view of the glove of FIG. 1 shown during removal from the left hand of a user by pulling the uncovered gripping means with the bare fingers of the right hand.
Figure 5:
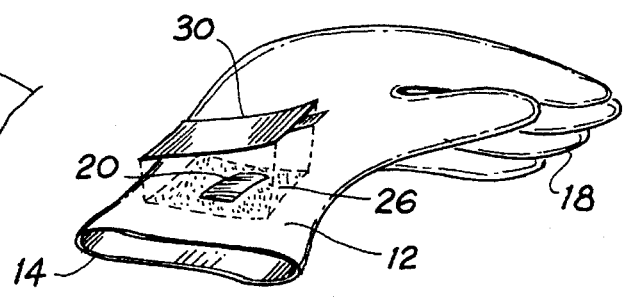
FIG. 5 is a view of the glove shown in FIG. 4 wherein the protective cover has been removed to expose clean gripping means.

Referring to the drawings, wherein like parts are designated throughout with like numerals and symbols, FIG. 1 illustrates in perspective view the preferred embodiment of a glove 10 that incorporates protected gripping means according to the present invention. While the glove 10 is illustrated and described with reference to a surgical glove, it is understood that any protective glove can be manufactured to comprise the features of the present invention, which is therefore not to be limited in scope to surgical applications. The glove 10 is made with elastomeric impermeable material, such as latex, to prevent fluid penetration from the exterior and avoid contamination of the skin of a wearer. As all conventional gloves, the glove 10 comprises a wrist portion 12 with an edge 14 adapted for wrapping tightly around the wrist of the wearer, so that penetration of contaminants between the glove and the wrist is prevented, and a hand portion 16 with individual fingers 18. The preferred gripping means consists of a glove tab 20 fixedly attached to the wrist portion and adapted for gripping by the fingers of the opposite hand of a user and for pulling toward the distal end of the gloved hand to remove the glove. The tab 20 is thus attached to the glove at one end, such as the proximal end 22 (proximal with respect to the gloved hand), and is free at the other end 24, so that it may be gripped and pulled to remove the glove 10, as illustrated in FIG. 2. Critical to this invention is a protective cover 30, which is adapted for covering the glove tab 20 and hermetically sealing it from outside contamination. This is achieved by providing a layer of bonding adhesive 26 in the area of the wrist portion 12 overlapped by the cover 30. The adhesive 26 is of a kind that permits permits a user to remove the protective cover 30 simply by pulling the cover off the glove and without damaging the wrist portion of the glove. A cover tab 32 may be provided to facilitate the removal operation. Preferably, the adhesive 26 is placed over the entire underside 34 of the cover 30 and over the corresponding overlapped area of the wrist portion of the glove, so that the glove tab 20 is fully sealed off and protected during use of the glove. Even more preferably, the outer portion of the tab 20 is also bonded to the cover 30 while the inner portion is free of adhesive, so that the motion of pulling out the protective cover 30 also results in raising the free end 24 of the glove tab 20, such that it is easier to grip and pull. Finally, the protective cover 30 may be permanently attached at one end to the wrist portion 12 of the glove, as illustrated in FIGS. 1–3, and remain dangling as a free flap after detachment, or it may constitute a separate detachable component, as shown in FIGS. 4 and 5. The latter embodiment is preferred because it allows the complete separation and disposal of the protective cover 30, which may be contaminated and could provide a source of infection if left dangling on the glove while the opposite ungloved hand is pulling on the glove tag 20 (as seen in FIG. 2).

Thus, in operation, the invention requires each glove to have a glove tab 20 and at least one of a pair of gloves to also comprise a protective cover 30. Where, for example, only the right glove is equipped with a protective cover 30, it is first removed by pulling the cover tab 32 with the gloved left hand. The glove tab 20 of the left glove is then gripped by the fingers of the gloved right hand and pulled to peel off and remove the left glove. Finally, the newly-exposed glove tab 20 of the right glove is gripped by the bare fingers of the ungloved left hand and pulled to peel it off and remove it.

Obviously, if both gloves are equipped with a protective cover 30, each gloved hand is first used to remove the protective cover from the other hand by pulling the cover tab 32. The rest of the procedure remains the same.

It is readily apparent that the glove of this invention provides a self-contained means for safely removing contaminated gloves after use by following the outlined procedure. One critical aspect of the invention is the impermeable feature of the bond between the protective cover and the glove in order to seal the gripping means 20 and prevent penetration of liquid contaminants. Accordingly, adhesives that require intimate contact between the glove and cover surfaces are acceptable, but fasteners that create a porous layer therebetween, such as Velcro® strips, would be unsafe and therefore are not adequate to practice the invention.

Figure 6:
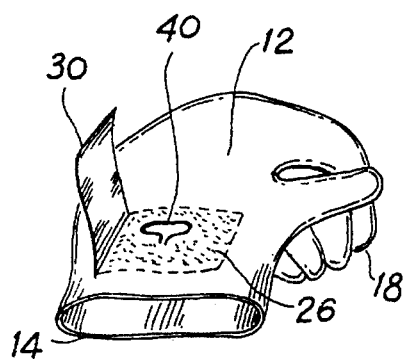
FIG. 6 a view of a loop embodiment of the gripping means of the invention.
Figure 7:
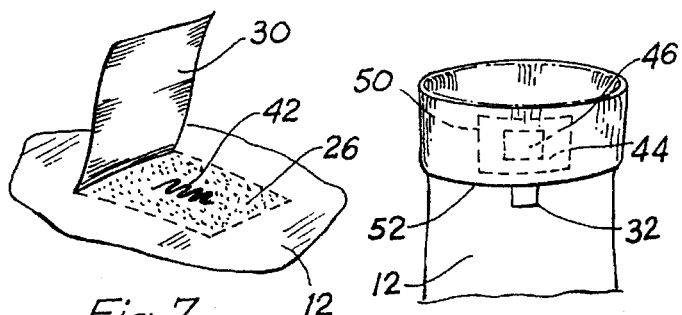
FIG. 7 a view of a string embodiment of the gripping means of the invention.
Figure 8:
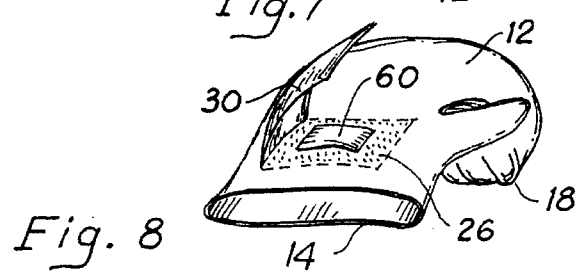
FIG. 8 a view of a finger-pocket embodiment of the gripping means of the invention.

The specific structure of the protective cover 30 and of the gripping means 20 may vary with different embodiments of the invention, so long as the functional characteristics are retained as described. For example, as illustrated in FIG. 6, the gripping means 20 may consist of a loop 40 (instead of a tab) attached to the glove and covered by the protective cover 30 by means of a bonding medium 26, as in the case of the preferred embodiment discussed above. Another gripping means may be simply a string 42 with an end attached to the wrist portion of the glove and similarly protected by the cover 30, as shown in the partial view of FIG. 7. Yet another gripping means may consist of a finger pocket 60 covered by the same gripping means 30, as illustrated in FIG. 8. The pocket 60 is uncovered and the glove is removed by inserting a finger in the pocket and pulling the glove distally. It is understood that these methods of implementing gripping means are for enablement purposes only and not intended to constitute a limitation on the scope of the invention. Any equivalent structure adapted for gripping by a user's hand and capable of being completely isolated by a protective cover would be suitable for praticing the invention.

Figure 9:
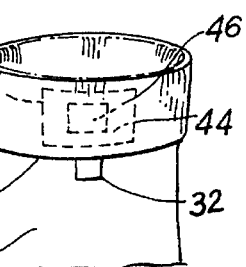
FIG. 9 a view of a cuff embodiment of the protective cover of the invention.

Similarly, the protective cover 30 of the invention may be implemented in different equivalent ways. For example, it may be integral with the wrist portion 12 of the glove of the invention, such as by constituting a cuff 44 folded outwardly from the edge 14 to overlap gripping means 46 (which could be any one of the disclosed means 20, 40, 42 and 60, or yet another equivalent means) sandwiched between the cuff and the glove, as illustrated in FIG. 9. A bonded area 50 would ensure intimate contact betwen the cuff and the glove to protect the gripping means 46 from contamination. A cover tab 32 could also be attached to the edge 52 of the cuff in alignment with the location of the gripping means to facilitate the lifting of the cuff to expose the gripping means at the time of removal of the glove.

Various changes in thee details, steps and materials that have been described may be made by those skilled in the art within the principles and scope of the invention herein illustrated and defined in the appended claims. Therefore, while the present invention has been shown and described herein in what is believed to be the most practical and preferred embodiment, it is recognized that departures can be made therefrom within the scope of the invention, which is therefore not to be limited to the details disclosed herein but is to be accorded the full scope of the claims so as to embrace any and all equivalent apparatus and methods.

What we claim is:

1. A glove with removal means protected from contamination to avoid exposure by a wearer while the glove is taken off, comprising:
   (a) a glove made with impermeable material and comprising a wrist portion adapted to prevent penetration of contaminants between the glove and a wrist of the wearer;
   (b) gripping means attached to an outer surface of said wrist portion and adapted for gripping and for pulling to remove the glove; and
   (c) protective-cover means for completely covering said gripping means and hermetically sealing it from contamination, said protective-cover means being attached to said outer surface of the wrist portion over an area surrounding said gripping means and being detachable such that said gripping means may be exposed for removing the glove.

2. The glove described in claim 1, wherein said glove is made with elastomeric material.

3. The glove described in claim 1, wherein said glove is made with latex.

4. The glove described in claim 1, wherein said gripping means consists of a tab.

5. The glove described in claim 1, wherein said gripping means consists of a loop.

6. The glove described in claim 1, wherein said gripping means consists of a string.

7. The glove described in claim 1, wherein said gripping means consists of a finger pocket.

8. The glove described in claim 1, wherein said protective-cover means comprises a cover tab to facilitate the detachment of the protective-cover means from the wrist portion of the glove to expose said gripping means.

9. The glove described in claim 1, wherein said protective-cover means is detachably bonded to said outer surface of the wrist portion of the glove by means of adhesive.

10. The glove described in claim 1, wherein said detachable protective-cover means comprises a side integral with said outer surface of the wrist portion of the glove.

11. The glove described in claim 1, wherein said detachable protective-cover means consists of a separate component removably attached to said outer surface of the wrist portion of the glove.

12. The glove described in claim 1, wherein said detachable protective-cover means consists of a portion of a cuff overlapping said outer surface of the wrist portion of the glove.

13. The glove described in claim 1, wherein said glove is made with elastomeric material, said gripping means consists of a tab, and said protective-cover means is detachably bonded to the outer surface of the wrist portion of the glove by means of adhesive and comprises a cover tab to facilitate the detachment of the protective-cover means from the wrist portion of the glove to expose said gripping means.

14. The glove described in claim 12, wherein said detachable protective-cover means consists of a separate component removably attached to the outer surface of the wrist portion of the glove.

15. The glove described in claim 12, wherein said detachable protective-cover means consists of a portion of a cuff overlapping the outer surface of the wrist portion of the glove.

16. A method for safely removing a contaminated glove after use, comprising the following steps:
   (a) providing and using a glove made with impermeable material and comprising a wrist portion adapted to prevent penetration of contaminants between the glove and a wrist of the wearer; said glove also comprising gripping means attached to an outer surface of said wrist portion and adapted for gripping and for pulling to remove the glove; and further comprising protective-cover means for completely covering said gripping means and hermetically sealing it from contamination, said protective-cover means being attached to said outer surface of the wrist portion over an area surrounding said gripping means and being detachable such that said gripping means may be exposed;
   (b) detaching said protective-cover means to expose said gripping means; and
   (c) using said gripping means to pull the glove off a wearer's hand;
      whereby said gripping means remains uncontaminated during use of the glove and may be safely touched during removal of the glove.

17. The method described in claim 16, wherein said gripping means consists of a tab.

18. The method described in claim 16, wherein said gripping means consists of a loop.

19. The method described in claim 16, wherein said gripping means consists of a string.

20. The method described in claim 16, wherein said gripping means consists of a finger pocket.

* * * * *